US00PP31202P2

(12) United States Plant Patent
Levac

(10) Patent No.: US PP31,202 P2
(45) Date of Patent: Dec. 10, 2019

(54) ***SORBARIA* PLANT NAMED 'LEVGREEN'**

(50) Latin Name: *Sorbaria sorbifolia*
Varietal Denomination: Levgreen

(71) Applicant: Denis Levac, St-Paul Joliette (CA)

(72) Inventor: Denis Levac, St-Paul Joliette (CA)

( * ) Notice: Subject to any disclaimer, the term of this patent is extended or adjusted under 35 U.S.C. 154(b) by 0 days.

(21) Appl. No.: 16/350,625

(22) Filed: Dec. 11, 2018

(51) Int. Cl.
*A01H 5/00* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 5/00
See application file for complete search history.

*Primary Examiner* — Kent L Bell
(74) *Attorney, Agent, or Firm* — Penny J. Aguirre

(57) ABSTRACT

A new cultivar of *Sorbaria sorbifolia* plant named 'Levgreen' that is characterized by its compact plant habit; reaching an average of 50 cm in height and 60 cm in width as a 5-year-old plant in the landscape, its non-suckering growth habit, its foliage that is bright green with a tinge of bronze on the leaves in summer, and its very sparse flowering habit.

2 Drawing Sheets

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

Botanical classification: *Sorbaria sorbifolia.*

Variety denomination: 'Levgreen'.

BACKGROUND OF THE INVENTION

The present invention relates to a new and distinct cultivar of *Sorbaria sorbifolia* and will be referred to hereafter by its cultivar name, 'Levgreen'. 'Levgreen' is a new cultivar of false spirea, a shrub grown for use as a landscape plant.

The new cultivar was discovered in summer of 2007 by the Inventor as a naturally occurring branch mutation of an unnamed plant of *Sorbaria sorbifolia* that was growing in a container in Ste-Therese, Quebec, Canada.

Asexual propagation of the new cultivar was first accomplished by the Inventor using stem cuttings in summer of 2008 in Ste-Therese, Quebec, Canada. Asexual propagation by stem cuttings and tissue culture initiated from meristematic tissue has determined that the characteristics of 'Levgreen' are stable and reproduced true to type in successive generations.

SUMMARY OF THE INVENTION

The following traits have been repeatedly observed and represent the characteristics of the new cultivar. These attributes in combination distinguish 'Levgreen' as a unique cultivar of *Sorbaria.*

1. 'Levgreen' exhibits a compact plant habit; reaching an average of 50 cm in height and 60 cm in width as a 5-year-old plant in the landscape.
2. 'Levgreen' exhibits a non-suckering growth habit.
3. 'Levgreen' exhibits foliage that is bright green with a tinge of bronze on the leaves in summer.
4. 'Levgreen' exhibits a very sparse flowering habit.

The parent plant of 'Levgreen' differs from 'Levgreen' in producing many suckers and in having a much taller plant height in reaching an average of 1.2 m in height as a 5-year-old plant and other typical plants of the species can reach a plant size of 1.8 m in height and 1.5 m in height and typically spread rapidly by suckers. 'Levgreen' can be most closely compared to the *Sorbaria sorbifolia* cultivar 'Sem' (U.S. Plant Pat. No. 16,336). 'Sem' differs from 'Levgreen' in spreading rapidly by suckers, having a larger plant size; reaching 1.5 m in height and 1.2 m in width in the landscape, and in having foliage that emerges pink to red, turns to chartreuse with bronze tips and then to green.

BRIEF DESCRIPTION OF THE DRAWINGS

The accompanying colored photographs illustrate the overall appearance and distinct characteristics of a two-year-old plant of the new *Sorbaria* as grown outdoors in a trial plot in Cottage Grove, Minn.

The photograph in FIG. 1 illustrates the overall appearance of 'Levgreen' in summer.

Figure 1:
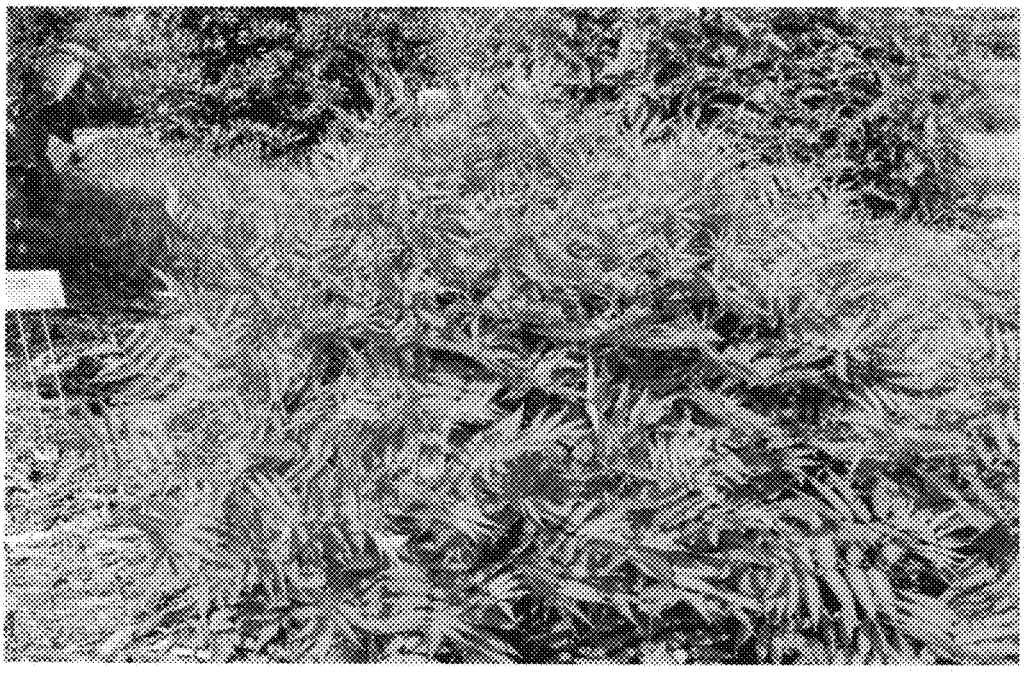
Figure 2:
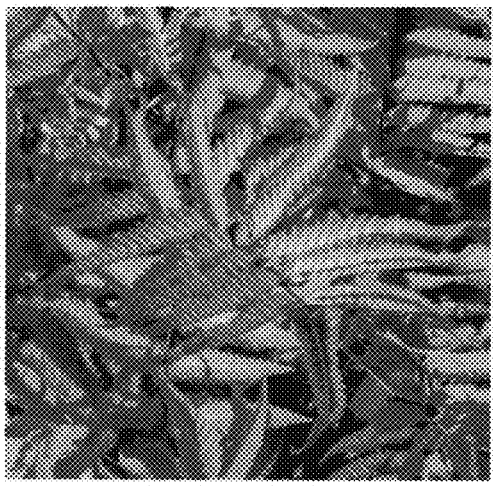

The photograph in FIG. 2 provides a close-up view of the summer foliage of 'Levgreen'.

Figure 3:
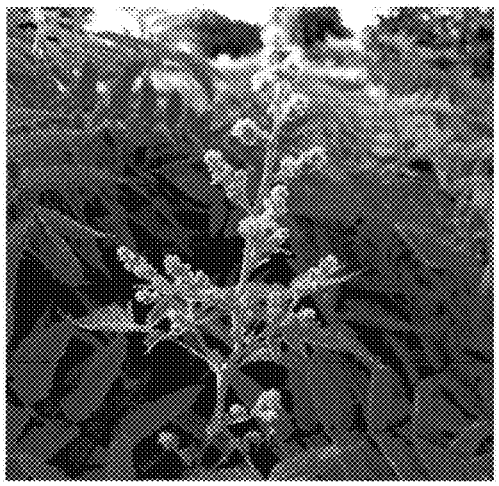

The photograph in FIG. 3 provides a view of an inflorescence in bud of 'Levgreen'.

Figure 4:
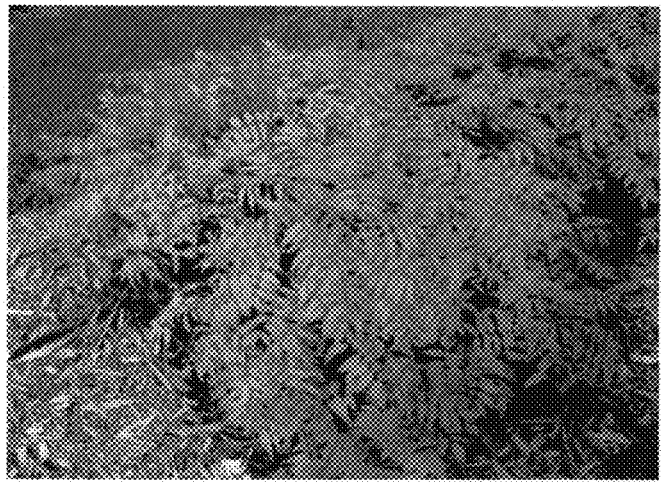

The photograph in FIG. 4 provides a view of 'Levgreen' in fall.

The colors in the photographs are as close as possible with the digital photography techniques utilized and the color values cited in the detailed botanical description accurately describe the colors of the new *Sorbaria*.

DETAILED BOTANICAL DESCRIPTION

The following is a detailed description of two-year-old plants of the new *Sorbaria* as grown outdoors in a trial plot in Cottage Grove, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Sparsely flowering for 3 to 4 weeks in July in Quebec, Canada.

*Plant type.*—Deciduous shrub, perennial.

*Plant habit.*—Upright, compact and outwardly spreading.

*Height and spread.*—Reaches an average of 50 cm in height and 60 cm in width as a 5-year-old plant in the landscape.

*Cold hardiness.*—At least to U.S.D.A. Zone 4.

*Diseases and pests.*—No resistance or susceptibility to diseases or pests has been observed.

*Root description.*—Fibrous, outward spreading by underground rhizomes has not been observed; observed to be non-suckering.

*Propagation.*—Stem cuttings or tissue culture.

*Root development.*—An average of 5 weeks for root development and a young rooted plant is produced in about 3 months.

*Growth rate.*—Slow.

Stem description:

*Stem strength.*—Strong.

*Stem shape.*—Rounded.

*Stem size.*—Average of 54 cm in length and 5 mm in width, base stems 1 cm in width.

*Stem surface.*—Young and mature stems are glabrous, matte and densely to moderately covered with lenticels; an average of 25 per 2 cm diameter, raised rounded, and 145C in color, old stems at base are dull, bark-like and rugose.

*Stem color.*—Young and mature stems; 145A, old stems; 199A and 165A.

*Stem aspect.*—Upright to slightly outward.

*Internode length.*—Average of 5 cm.

*Stem quantity.*—Average of 5 to 10 per plant.

*Branching.*—Basal stems grow from the base.

Foliage description:

*Leaf/leaflet shape.*—Whole leaf; ovate overall, leaflet; lanceolate.

*Leaf division.*—Compound.

*Leaf/leaflet arrangement.*—Leaf; alternate, leaflet; opposite.

*Leaf/leaflet attachment.*—Leaf; petiolate, leaflet; sessile.

*Leaf/leaflet quantity.*—Average of 16 leaves per branch, 15 leaflets per leaf.

*Leaflet base.*—Cordate.

*Leaflet apex.*—Acuminate.

*Leaflet fragrance.*—None.

*Leaflet venation.*—Pinnate, upper surface; in spring 145A, in summer mature leaves become heavily suffused with 178A, lower surface; mid-rib is slightly protruding on lower surface 145C, in summer mature leaves become 146A, flushed with 178A.

*Leaflet margins.*—Doubly surrate.

*Leaflet sinus.*—Average of 5 mm in depth when mature, 0.5 mm in depth when young.

*Leaflet surface.*—Both surfaces dull and glabrous.

*Leaf/leaflet size.*—Leaf; average of 18 cm in length and 13 cm in width, leaflet; 7 cm in length, 2 cm in width.

*Leaflet color.*—Young upper surface; in spring NN137A, in summer 144A, heavily suffused with 176A, young lower surface; in spring N138B, in summer 144A, heavily suffused with 178A, mature upper surface; in spring NN137B, in summer 146A, undertones of 145A, mature lower surface; in spring NN137C, in summer 146A, in fall all leaves upper and lower surface; 144C and 142A, leaves become flushed with 153A and suffused with 175A.

*Petioles.*—Average of 2.5 cm in length and 2 mm in diameter, color 185A on upper surface and 146B on lower surface, surface is slightly shiny, sparsely covered with short hairs that match surface color, slightly flattened in shape.

*Rachis.*—2 cm in length, 2 mm in width, other characteristics similar to petiole.

*Stipules.*—2 at each petiole base, cuneate base, average of 2 mm in length, 1 mm in width, matches leaflet surface colors, acute apex, linear to lanceolate in shape, margins serrated and densely covered with woolly pubescence, both surfaces dull.

Inflorescence description:

*Inflorescence type.*—Dense umbellate corymbs, present at terminus of lateral branches.

*Inflorescence size.*—Average of 9 cm in diameter and 15 cm in depth.

*Peduncles.*—Average of 5 cm in length and 1 mm in width, 145A, flushed with 173A in color, surface is shiny and sparsely covered with short white hairs that match surface, moderate strength.

*Pedicels.*—Average of 1.5 cm in length and 0.5 mm in width, 145A, flushed with 173A in color, surface is shiny and sparsely covered with short white hairs that match surface, moderate strength.

*Flower buds.*—Oval in shape, 1 mm in depth and diameter, 145A in color.

*Persistence of flowers.*—Calyx persistent.

*Flower quantity.*—Average of 50 per peduncle, 500 per inflorescence.

*Lastingness of flowers.*—Each inflorescence lasts an average of 10 days with individual flowers lasting an average of 2 days.

*Flower type.*—Rotate with numerous extended stamens.

*Flower aspect.*—Inflorescence held upright on stem terminus.

It is claimed:

1. A new and distinct cultivar of *Sorbaria* plant named 'Levgreen' as herein illustrated and described.

* * * * *